(12) United States Patent
Qian et al.

(10) Patent No.: US 11,221,286 B2
(45) Date of Patent: Jan. 11, 2022

(54) METHOD FOR DETECTING COMPACTION AND SHEAR STRENGTH CHARACTERISTICS OF ASPHALT MIXTURE DURING CONSTRUCTION COMPACTION

(71) Applicant: Changsha University of Science and Technology, Changsha (CN)

(72) Inventors: Guoping Qian, Changsha (CN);
Huanan Yu, Changsha (CN);
Changyun Shi, Changsha (CN);
Xiangbing Gong, Changsha (CN); Xi Li, Changsha (CN); Jun Cai, Changsha (CN); Wenchao Wu, Changsha (CN)

(73) Assignee: CHANGSHA UNIVERSITY OF SCIENCE AND TECHNOLOGY, Changsha (CN)

( * ) Notice: Subject to any disclaimer, the term of this patent is extended or adjusted under 35 U.S.C. 154(b) by 79 days.

(21) Appl. No.: 16/880,436

(22) Filed: May 21, 2020

(65) Prior Publication Data
US 2021/0088430 A1 Mar. 25, 2021

(30) Foreign Application Priority Data
Sep. 19, 2019 (CN) .......................... 201910884633.6

(51) Int. Cl.
*G01N 3/24* (2006.01)
*G01N 3/06* (2006.01)
(Continued)

(52) U.S. Cl.
CPC .............. *G01N 3/24* (2013.01); *G01N 3/066* (2013.01); *G01N 33/42* (2013.01); *E01C 23/01* (2013.01);
(Continued)

(58) Field of Classification Search
CPC ........... G01N 3/24; G01N 3/066; G01N 3/22; G01N 33/42; G01N 2203/0003;
(Continued)

(56) References Cited

PUBLICATIONS

He Jianxin, Qiu Ming. Control of asphalt pavement compaction [J], Science and Technology, 2010 (15) 216.
(Continued)

*Primary Examiner* — Jonathan M Dunlap
(74) *Attorney, Agent, or Firm* — Brundidge & Stanger, P.C.

(57) ABSTRACT

The present invention discloses a method for detecting compaction and shear strength characteristics of an asphalt mixture during construction compaction. The method mainly includes the following steps: using a device for detecting compaction and shear strength characteristics of the asphalt mixture; pressing a test claw into the asphalt mixture during construction; rotating the test claw slowly and uniformly to measure an internal temperature and a shear characteristic of the mixture during paving and subsequent compaction; calculating a corresponding compaction detection index based on the shear characteristic; and monitoring and guiding the construction quality and construction process accordingly based on the real-time detection index. The present invention measures the compaction detection index of the asphalt mixture during compaction simply, quickly and accurately. The present invention uses the compaction detection index together with a degree of compaction for dual control of asphalt pavement compaction.

2 Claims, 2 Drawing Sheets

(51) Int. Cl.
*G01N 33/42* (2006.01)
*G01N 3/22* (2006.01)
*E01C 23/01* (2006.01)

(52) U.S. Cl.
CPC ....... *G01N 3/22* (2013.01); *G01N 2203/0003* (2013.01); *G01N 2203/003* (2013.01); *G01N 2203/0021* (2013.01); *G01N 2203/0025* (2013.01); *G01N 2203/0085* (2013.01); *G01N 2203/0248* (2013.01); *G01N 2203/0256* (2013.01)

(58) Field of Classification Search
CPC ..... G01N 2203/0025; G01N 2203/003; G01N 2203/0085; G01N 2203/0248; G01N 2203/0021; G01N 2203/0256; E01C 23/01
See application file for complete search history.

(56) References Cited

PUBLICATIONS

Sun Bo. Current situation and measures of compaction control of expressway asphalt pavement [J], Communications Science and Technology Heilongjiang, 20.
Goodman S N, Hassan Y, El Halim A E H. Shear properties as viable measures for characterization of permanent deformation of asphalt concrete mixtures [.
Gudimettla J M, Cooley Jr L A, Brown E R. Workability of hot-mix asphalt [J], Transportation research record, 2004, 1891(1) 229-237.
Zhang Zhengqi, Bian Xiuqi, Du Qunle, et al. Study on factors effecting on compaction property of asphalt mixture [J], Journal of Wuhan University of Te.
Tang Wen, Sun Lijun. Shear resistance performance of asphalt mixture at different temperature and its evaluation indexes [J] Highway, 2012 (3) 191-195.
Shi Hangqi. Research on compaction workability of asphalt mixture by using shear compactor [D].

METHOD FOR DETECTING COMPACTION AND SHEAR STRENGTH CHARACTERISTICS OF ASPHALT MIXTURE DURING CONSTRUCTION COMPACTION

TECHNICAL FIELD

The present invention belongs to the technical field of asphalt mixture compaction detection, and relates to a method for detecting compaction and shear strength characteristics of an asphalt mixture during construction compaction. The detection method is used to evaluate the compaction quality of the asphalt mixture, and to monitor and guide the construction quality and construction process accordingly based on real-time detection results.

BACKGROUND

Compaction is the last step in the formation of asphalt pavement. Construction compaction control is a necessary method to ensure that the quality, physical and mechanical properties and pavement performance of asphalt mixture meet requirements. China's technical specifications for asphalt pavement construction specify the compaction control index and method of asphalt pavement, as well as the detection location, frequency and allowable deviation, etc. A traditional compaction detection index is the degree of compaction of pavement.

In 2010, He Jianxin and Qiu Ming et al. [1] pointed out that the use of a single simple compaction index for compaction control is not comprehensive, and it should be combined with other characteristics of asphalt mixture and pavement. In 2017, Sun Bo [2] analyzed the development status of compaction control of expressway pavement, and pointed out that asphalt pavement had different asphalt-aggregate ratios at different levels and the mixing of asphalt mixture is largely variable. Therefore, he believed that it was not sufficiently stable to use a single degree of compaction for control, which would cause a large potential quality hazard.

Traditional compaction detection methods include sand filling method, water bag method, cutting ring method, wax seal method and nuclear density gage method, etc. However, these construction control methods are mainly used for detection in a construction acceptance stage. The detection is post-construction detection, lagging behind the compaction process. Therefore, over- and under-compaction sections cannot be found in time. The combination of compaction machinery and compaction times at the construction site are generally determined by experience. It is impossible to adjust and control the construction process and construction quality according to detection results. Due to the lack of proper asphalt mixture compaction status detection devices and methods, there are difficulties in quality supervision and construction process control.

In 2002, Stephen N. Goodman and Yasser Hassan et al. [3] proposed that shear strength was a feasible measure to characterize the permanent deformation of asphalt concrete. They used an in-situ shear stiffness test (InSiSST) facility developed by Carleton University to analyze the shear-strength-related characteristics of the mixture, including binder property, binder amount and aggregate characteristics (type, grading, etc.). However, this study is only applicable to post-construction detection of pavements after open traffic, and is difficult to apply to on-line construction detection.

In 2004, Jagan M. Gudimettla and L. Allen cooley, Jr et al. [4] tested workability test equipment and evaluated the workability of the asphalt mixture by applying a torque to a crosshead inserted into the asphalt mixture before paving. The test results showed that different factors had largely different effects on the compactability of asphalt mixture. These factors included asphalt binder characteristics, mixture temperature, aggregate type and nominal maximum size of aggregate in a descending order of their effects. This equipment could only measure the torque of asphalt mixture. The study did not show a direct correlation between the workability and compaction of asphalt mixture, and is not suitable for compaction detection during the construction stage.

In 2005, China's professor Zhang Zhengqi [5] used multiple groups of asphalt mixtures for laboratory gyratory compaction analysis. He proposed to use a compact energy index of a compaction curve from an initial compaction status to design compaction times to evaluate the compactability of asphalt pavement. However, due to a boundary problem, this study is difficult to determine the compaction energy of site construction, and cannot be directly used for construction guidance.

In 2012, Tang Wen and Sun Lijun et al. [6] studied the changing shear strength of asphalt mixture at different temperatures. They found a good correlation between different shear evaluation indexes through different shear strength tests. Their study showed that temperature had a great influence on the shear strength of asphalt mixture and the temperature characteristics of asphalt mixture should be fully considered to evaluate the shear strength thereof.

In 2017, Shi Hangqi and Xu Shifa et al. [7] from Beijing University of Civil Engineering and Architecture used a laboratory shear compactor to form an asphalt mixture. They further explored the compaction and shear strength characteristics of the mixture to obtain a corresponding workable compaction temperature under the use of the shear compactor. They proposed to use a compaction shear stress index to evaluate the compaction performance of the mixture and analyzed the feasibility of using shear strength to evaluate the compaction status of the mixture. However, due to the complexity of the equipment, this study is difficult to use for on-site mixture compaction detection.

Great progress have been made in the compaction detection methods of asphalt mixture at home and abroad. However, most of the current research still focuses on the post-construction compaction detection of asphalt mixture, and online detection has not been realized. Therefore, it is impossible to adjust and control the construction process and construction quality according to detection results. At present, there is a lack of a device for detecting the compaction status of the asphalt mixture during on-site construction compaction. Therefore, it is necessary to further research the real-time detection of compaction quality and research the evaluation indexes and standards of the asphalt mixture.

CITED REFERENCES

[1] He Jianxin, Qiu Ming. Control of asphalt pavement compaction [J]. Science and Technology, 2010 (15): 216.

[2] Sun Bo. Current situation and measures of compaction control of expressway asphalt pavement [J]. Communications Science and Technology Heilongjiang, 2017, 40 (7): 76-77.

[3] Goodman S N, Hassan Y, El Halim A E H. Shear properties as viable measures for characterization of permanent deformation of asphalt concrete mixtures [1]. Transportation research record, 2002, 1789(1): 154-161.

[4] Gudimettla J M, Cooley Jr L A, Brown E R. Workability of hot-mix asphalt [J]. Transportation research record, 2004, 1891(1): 229-237.

[5] Zhang Zhengqi, Bian Xiuqi, Du Qunle, et al. Study on factors effecting on compaction property of asphalt mixture [J]. Journal of Wuhan University of Technology, 2012, 34 (6): 36-41.

[6] Tang Wen, Sun Lijun. Shear resistance performance of asphalt mixture at different temperature and its evaluation indexes [J]. Highway, 2012 (3): 191-195.

[7] Shi Hangqi. Research on compaction workability of asphalt mixture by using shear compactor [D].

SUMMARY

In view of the technical shortcomings that the use of a single degree of compaction has insufficient stability and large quality hazard, an objective of the present invention is to provide a method for detecting compaction and shear strength characteristics of an asphalt mixture during construction compaction. The method measures a compaction detection index of the asphalt mixture during compaction simply, quickly and accurately. The method is used to accurately evaluate a compaction effect of the asphalt mixture, determine a compaction status of the asphalt mixture during a construction process, and adjust and control the construction process and construction quality according to a detection result in time.

The present invention provides a method for detecting compaction and shear strength characteristics of an asphalt mixture during construction compaction, including the following steps:

step 1: the asphalt mixture is paved on site; after the asphalt mixture is compacted by a compactor, a detection device is moved to a selected detection point;

step 2: a claw-shaped blade on an output end of a test claw is pressed into the asphalt mixture with a certain degree of compaction through a lift switch;

step 3: a power switch of an electric motor is turned on; the electric motor drives the test claw to rotate slowly and uniformly; a temperature T (° C.) and a torque M (N·m) on a display are recorded;

step 4: the torque M obtained in step 3 is used to calculate a shear strength and a shear stiffness of the asphalt mixture:

$$F = G\gamma = \frac{M\rho}{I_p} \quad G = \frac{F}{\gamma} = \frac{M\rho}{\gamma I_p}$$

where, F is the shear strength, G is the shear stiffness, $\gamma$ is a shear strain, $\rho$ is a radius, and $I_p$ is a polar moment of inertia; and step 5: the shear strength and the shear stiffness obtained in step 4 are used to calculate a compaction detection index $K/K_{min}$ of the asphalt mixture, where K is defined as an inverse of the shear stiffness, $$K = \frac{1}{G},$$

and $K_{min}$ is a minimum value of K of the asphalt mixture under a corresponding degree of compaction.

Preferably, in step 3, the rotation speed is 5°/min to 10°/min.

The detection device immediately detects the compaction status of a pavement with a certain degree of compaction on a construction site during a compaction process to obtain a compaction detection index $K/K_{min}$ of the asphalt mixture. As a mechanical index indicating the compaction status of the pavement, $K/K_{min}$ is closely related to the pavement's long-term fatigue life, rutting resistance and crack resistance. The detection device compares the compaction detection index $K/K_{min}$ obtained in real time with a standard value to determine the compaction status of the asphalt mixture based on the degree of compaction, so as to adjust and control the construction process and construction quality in time. The standard value is obtained by using the detection device and method of the present invention to repeatedly detect the design asphalt mixture and acquire and calibrate the data in a design stage. When a value of $K/K_{min}$ is greater than a right end value of the standard interval, a section is under-compacted and supplementary compaction construction should be implemented in time. When the value of $K/K_{min}$ is smaller than a left end value of the standard interval, the section is over-compacted and a remedial measure for over-compaction should be taken in time. When the value of $K/K_{min}$ is within the range of the standard interval, the compaction of the section is completed and a next stage of construction may be implemented. In an actual detection process, the blade of the test claw rotates relatively slow and the asphalt mixture has a certain self-healing property at a high temperature. Therefore, when the blade of the test claw is pressed into a constructed pavement for detection, it does not cause large damage to the pavement. The real-time detection data is instructive to a subsequent construction process, and can be used to prevent and remedy under- and over-compaction conditions to ensure a good compaction effect of the asphalt mixture.

In the present invention, the method for detecting compaction and shear strength characteristics of an asphalt mixture during construction compaction of adopts a detection device. The detection device specifically includes a fixed frame and a detection system. A universal wheel is arranged at the bottom of the fixed frame to facilitate a free movement for on-site construction detection. The detection system includes a display, a control panel, a test claw, an electric motor for driving the test claw to rotate, a lift switch for controlling a vertical movement of the test claw, a torque sensor and a temperature sensor. The control panel includes a power switch for controlling the electric motor and a speed regulator for controlling a rotation speed of the test claw. An output end of the electric motor is connected to an input end of the torque sensor, and an output end of the torque sensor is connected to an input end of the test claw. An output end of the test claw is provided with a claw-shaped blade. There are 3-6 claws of the claw-shaped blade. The bottom of the claw-shaped blade is a conical tip, which is convenient for pressing into the asphalt mixture with a certain degree of compaction. The claw-shaped blade is provided therein with the temperature sensor.

Compared with the prior art, the present invention has the following advantages:

1. The present invention tests accurately, and realizes dual control by the compaction process and the compaction index of actual construction. The present invention makes up for the shortcoming of using a single degree of compaction for control in conventional pavement construction compaction. The present invention accurately determines the compaction status of the asphalt mixture on site based on both the compaction detection index and the degree of compaction. The present invention detects the degree of compaction, tests the compaction detection index, and compares the compaction detection index obtained in real time with a standard value to accurately evaluate the compaction effect of the asphalt mixture. The present invention determines the compaction status of the asphalt mixture during the construction process, and adjusts and controls the construction process and construction quality in time according to a detection result.

2. The present invention tests fast in real time and provides immediate guidance for an actual construction compaction process. The compaction detection index of the asphalt mixture is measured in real time during the construction compaction process. Based on the compaction detection index obtained in real time on site, the detection method monitors the compaction status of the mixture in real time and guides the on-site construction in time. The detection method prevents and remedies under- and over-compaction conditions to ensure a good compaction effect of the asphalt mixture.

3. The present invention is simple and implementable. The present invention is directly used on a construction site for construction detection to realize real-time compaction control of the asphalt mixture. In a specific implementation process, the detection device is directly transported to the construction site. The detection device tests the asphalt mixture with a certain degree of compaction during post-paving and subsequent compaction to obtain the compaction detection index of the asphalt mixture in the construction process.

4. The present invention directly tests the asphalt mixture. In a practical application, the test claw is rotated slowly and uniformly to obtain a torque to measure the compactability of the mixture in actual construction. The slow rotation protects the asphalt pavement from large damage. The shear strength and shear stiffness of the asphalt mixture obtained during compaction directly reflect the mechanical properties of the asphalt mixture during construction. In addition, the present invention can also evaluate the compaction status of the asphalt mixture according to the calculated compaction detection index.

5. The present invention has a simple and reasonable structure and a wide range of applications, and is detectable for various types of asphalt mixtures. The present invention accurately reflects a compaction viscosity resistance of the asphalt mixture through the mixing of the asphalt mixture, which is expressed in the form of a torque. Then the present invention obtains the shear strength and shear stiffness of the asphalt mixture during compaction to directly reflect the mechanical properties of the asphalt mixture during construction. On this basis, the present invention determines whether to perform timely supplementary compaction. The present invention realizes accurate and immediate detection of the compaction status of asphalt mixtures with different proportions. Therefore, the present invention has universality and can be popularized in asphalt pavement construction.

Figure 1:
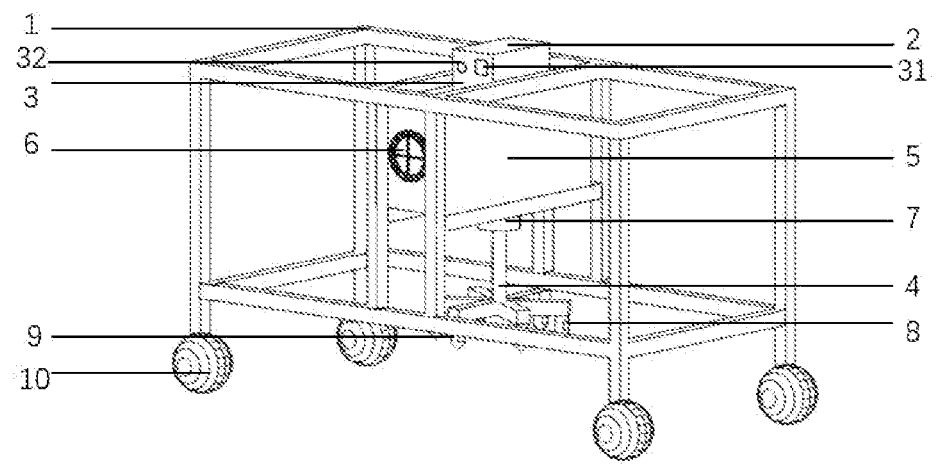
FIG. 1 is a structural diagram of a detection device for a method for detecting compaction and shear strength characteristics of an asphalt mixture during construction compaction according to the present invention.

Reference numerals: 1. fixed frame; 2. display; 3. control panel; 31. power switch; 32. speed regulator; 4. test claw; 5. electric motor; 6. lift switch; 7. torque sensor; 8. temperature sensor; 9. claw blade; and 10. universal wheel.

DETAILED DESCRIPTION

To make the technical means, creative features, purpose of use and effects of the present invention comprehensible, the present invention is further described blow with reference to the specific implementations.

Figure 2:
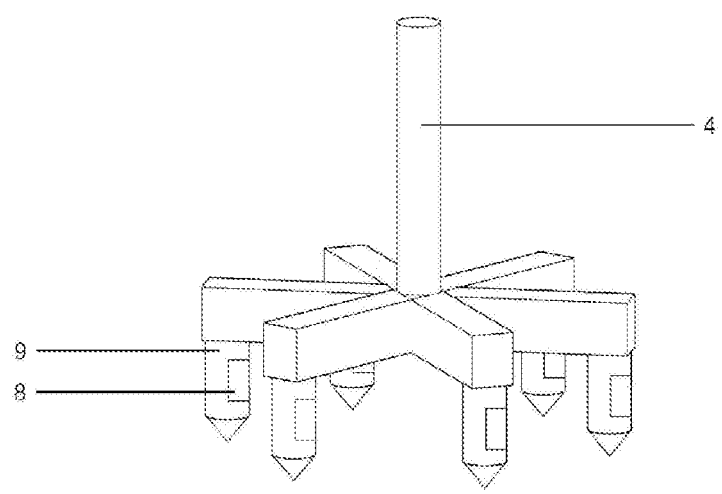
FIG. 2 is a structural diagram of a test claw.

Referring to FIG. 1 and FIG. 2, the present invention provides a device for detecting compaction and shear strength characteristics of an asphalt mixture during construction compaction. The device includes a fixed frame 1 and a detection system. A universal wheel 10 is arranged at the bottom of the fixed frame 1 to facilitate a free movement for on-site construction detection. The detection system includes a display 2, a control panel 3, a test claw 4, an electric motor 5 for driving the test claw 4 to rotate, a lift switch 6 for controlling a vertical movement of the test claw 4, a torque sensor 7 and a temperature sensor 8. The control panel 3 includes a power switch 31 for controlling the electric motor 5 and a speed regulator 32 for controlling a rotation speed of the test claw 4. An output end of the electric motor 5 is connected to an input end of the torque sensor 7, and an output end of the torque sensor 7 is connected to an input end of the test claw 4. An output end of the test claw 4 is provided with a claw-shaped blade 9. There are 6 claws of the claw-shaped blade 9. The bottom of the claw-shaped blade is a conical tip, which is convenient for pressing into the asphalt mixture with a certain degree of compaction. The claw-shaped blade is provided therein with the temperature sensor 8.

Figure 3:
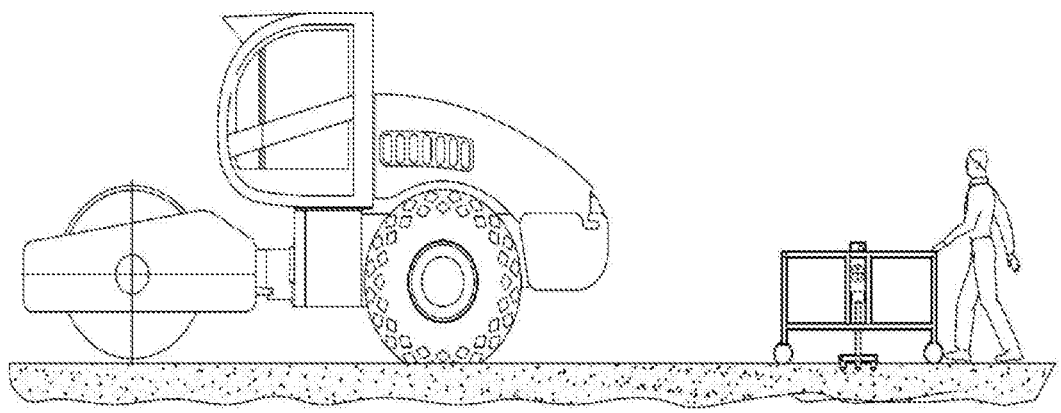
FIG. 3 is a diagram showing the use of a device for detecting compaction and shear strength characteristics of an asphalt mixture on a construction site.

As shown in FIG. 3, a specific process is as follows:

step 1: surface, intermediate and base courses of the asphalt mixture are paved separately on site; after the base course is compacted by a compactor, the detection device is moved to a selected detection point, and the universal wheel is fixed;

step 2: the claw-shaped blade on the output end of the test claw is pressed into the asphalt mixture with a certain degree of compaction through a lift switch;

step 3: the power switch of the electric motor is turned on; the electric motor drives a stirring shaft to rotate slowly and uniformly with a speed freely selected between 5°/min and 10°/min; a temperature T (° C.) and a torque M (N·m) on the display are recorded;

step 4: the torque M obtained in step 3 is used to calculate a shear strength and a shear stiffness of the asphalt mixture:

$$F = G\gamma = \frac{M\rho}{I_p} \quad G = \frac{F}{\gamma} = \frac{M\rho}{\gamma I_p}$$

where, F is the shear strength, G is the shear stiffness, $\gamma$ is a shear strain, $\rho$ is a radius, and $I_p$ is a polar moment of inertia; and step 5: the shear strength and the shear stiffness obtained in step 4 are used to calculate a compaction detection index $K/K_{min}$ of the asphalt mixture, where K is defined as an inverse of the shear stiffness, $$K = \frac{1}{G},$$

and $K_{min}$ is a minimum value of K when the asphalt mixture is correspondingly compacted; the compaction detection index $K/K_{min}$ obtained in real time is compared with a standard interval of $K/K_{min}$ in Standard Table 1 to determine the compaction status of the asphalt mixture, so as to adjust and control the construction process and construction quality in time; when a value of $K/K_{min}$ is greater than a right end value of the standard interval, a section is under-compacted and supplementary compaction construction should be implemented in time; when the value of $K/K_{min}$ is smaller than a left end value of the standard interval, the section is over-compacted, and a remedial measure for over-compaction should be taken in time; when the value of $K/K_{min}$ is within the range of the standard interval, the compaction of the base course is completed and steps 1-5 may be repeated to construct the intermediate and surface courses.

The corresponding values of the compaction detection index $K/K_{min}$ and the degree of compaction in Table 1 are standard values obtained by using the detection device and method of the present invention to repeatedly test the design asphalt mixture (AC-13C asphalt mixture herein) and acquire and calibrate the data in a design stage. It should be noted that the values in the standard table may vary with different design asphalt mixtures in actual engineering, but the detection device and method used are essentially unchanged. The degree of compaction is a ratio of a density of the asphalt mixture to a maximum theoretical density thereof. For a test method, refer to JTG F40-2017 "Technical Specifications for Construction of Highway Asphalt Pavement".

TABLE 1

Standard table of compaction detection index $K/K_{min}$ and degree of compaction for dual control

| Degree of compaction | | 0.8 | 0.82 | 0.84 | 0.86 | 0.88 | 0.9 | 0.92 | 0.94 | 0.96 | 0.98 |
|---|---|---|---|---|---|---|---|---|---|---|---|
| $K/K_{min}$ | Left end value | 0.8 | 0.82 | 0.84 | 0.85 | 0.86 | 0.87 | 0.88 | 0.88 | 0.9 | 0.9 |
| | Right end value | 2.2 | 2.0 | 1.8 | 1.7 | 1.6 | 1.5 | 1.4 | 1.3 | 1.2 | 1.2 |

Embodiment 1

In this embodiment, for example, an AC-13C asphalt mixture in a surface course is under a post-paving state. Three compactors are used to compact a section with a compaction method as shown in Table 2.

TABLE 2

Compaction method of section

| Compaction step | Primary compaction | Secondary compaction | Final compaction |
|---|---|---|---|
| Type of compactor | Steel drum compactor | Vibratory compactor | Steel drum compactor |
| Compaction speed (km/h) | 3 | 4 | 5 |
| Compaction times | 2 | 2 | 3 |

A compactor follows a paver to perform primary compaction. After static compaction by a steel drum compactor, a nuclear-free density gage is used to measure a degree of compaction of the asphalt mixture. Compaction and shear strength characteristics detection device is used to measure a real-time compaction detection index $K/K_{min}$ and an internal temperature T of the mixture. An electric motor drives a stirring shaft to rotate slowly and uniformly. A rotation speed is freely selected from 5°/min to 10°/min. The detection indexes of the compaction status are shown in Table 3.

TABLE 3

Detection indexes of primary compaction status of section

| Stake No. | Internal temperature of mixture °C. | Degree of compaction /% | $K/K_{min}$ |
|---|---|---|---|
| K2 + 060 | 127.1 | 82 | 1.96 |
| K2 + 080 | 129.9 | 86 | 1.24 |
| K2 + 100 | 126.2 | 84 | 1.27 |

The purpose of the primary compaction is to level and stabilize the mixture, while creating a condition for secondary compaction. After the primary compaction is completed, the degree of compaction of the mixture reaches more than 80%, and the primary compaction temperature is maintained at 110-130° C., which is a normal construction temperature. The degree of compaction and the compaction and shear strength characteristics index $K/K_{min}$ are compared with a standard value in Table 1. The degree of compaction is greater than a design degree of compaction (80%), and the compaction detection index $K/K_{min}$ of the asphalt mixture in each section is in the range of a standard interval. The degree of compaction and the compaction detection index both are acceptable, indicating that the primary compaction of the mixture is in good status and a next stage of construction may be implemented.

The secondary compaction follows the primary compaction. The secondary compaction is a key step for the compaction, stabilization and formation of the mixture. After the secondary compaction is completed with a vibratory compactor, the compaction performance of the asphalt mixture is detected the same as that in the primary compaction step. The detection indexes of the compaction status are shown in Table 4.

TABLE 4

Detection indexes of secondary compaction status of section

| Stake No. | Internal temperature of mixture °C. | Degree of compaction /% | $K/K_{min}$ |
|---|---|---|---|
| K2 + 060 | 108.2 | 97 | 1.02 |
| K2 + 080 | 110.6 | 95 | 1.24 |
| K2 + 100 | 90.4 | 86 | 1.84 |

For section K2+060, the internal temperature of the mixture is 108.2° C.; the degree of compaction and the compaction and shear strength characteristics index of the mixture are consistent with those in Table 1. This indicates that the compaction of the mixture is in good status and a next stage of construction may be implemented.

For section K2+080, the temperature of the mixture is 110.6° C. The degree of compaction under this temperature meets a design requirement. The detection index $K/K_{min}$ of the mixture is 1.24, which is greater than a normal value of 1.20 under a corresponding degree of compaction (95%). This indicates that the internal mechanical property of the mixture is not up to standard, and the compaction of the mixture is unqualified. The following methods may be used to improve the mechanical property of the mixture:

1. replace the vibratory compactor with a tire compactor to knead the mixture to reduce the friction between particles and allow a small particle to enter a gap between large particles; and 2. slow down the compaction of the vibratory compactor and increase the contact time between the compactor and the mixture; or adopt a high-frequency large-amplitude method to generate a large excitation force.

For section K2+100, the degree of compaction after the secondary compaction is too small. The detection index $K/K_{min}$ of the mixture is 1.84, which is greater than a normal value of 1.70 under a corresponding degree of compaction (86%), indicating that the compaction of the section is not qualified. The internal temperature of the mixture is 90.4° C., which is lower than a normal secondary compaction temperature (95-115° C.). Therefore, remedial construction cannot be performed. In this case, if compaction is continued, it will cause insufficient compaction of the section, and it will easily cause problems such as rutting and peeling in long-term use. Therefore, it is recommended that the section be scrapped and repaved.

What is claimed is:

1. A method for detecting compaction and shear strength characteristics of an asphalt mixture during construction compaction, comprising the following steps:

step 1: the asphalt mixture is paved on site; after the asphalt mixture is compacted by a compactor, a detection device is moved to a selected detection point;

step 2: a claw-shaped blade on an output end of a test claw is pressed into the asphalt mixture with a certain degree of compaction through a lift switch;

step 3: a power switch of an electric motor is turned on; the electric motor drives the test claw to rotate slowly and uniformly; a temperature T (° C.) and a torque M (N·m) on a display are recorded;

step 4: the torque M obtained in step 3 is used to calculate a shear strength and a shear stiffness of the asphalt mixture:

$$F = G\gamma = \frac{M\rho}{I_p} \quad G = \frac{F}{\gamma} = \frac{M\rho}{\gamma I_p}$$

wherein, F is the shear strength, G is the shear stiffness, $\gamma$ is a shear strain, $\rho$ is a radius, and $I_p$ is a polar moment of inertia; and step 5: the shear strength and the shear stiffness obtained in step 4 are used to calculate a compaction detection index $K/K_{min}$ of the asphalt mixture, wherein K is defined as an inverse of the shear stiffness, $$K = \frac{1}{G},$$

and $K_{min}$ is a minimum value of K of the asphalt mixture under a corresponding degree of compaction.

2. The method for detecting compaction and shear strength characteristics of an asphalt mixture during construction compaction according to claim 1, wherein in step 3, the rotation speed is 5°/min to 10°/min.

* * * * *